United States Patent [19]

Ninagawa et al.

[11] 4,006,193
[45] Feb. 1, 1977

[54] ISOMERIZATION OF THE UNSATURATED ALCOHOLS

[75] Inventors: Yoichi Ninagawa; Takashi Nishida; Kazuo Itoi, all of Kurashiki, Japan

[73] Assignee: Kuraray Co., Ltd., Kurashiki, Japan

[22] Filed: Mar. 12, 1973

[21] Appl. No.: 340,585

[30] Foreign Application Priority Data

June 14, 1972 Japan .............................. 47-59183
Mar. 13, 1972 Japan .............................. 47-26017
June 14, 1972 Japan .............................. 47-59182

[52] U.S. Cl. .................. 260/617 R; 252/431 R; 260/631.5; 260/632 R; 260/642 R
[51] Int. Cl.² .......................................... C07C 33/02
[58] Field of Search ............. 260/617 R, 631.5, 632

[56] References Cited

FOREIGN PATENTS OR APPLICATIONS 1,599,581  7/1970  France ............................ 260/617 R
1,965,377  7/1976  Germany .......................... 260/631
1,256,184  12/1971 United Kingdom ............ 260/617 R

OTHER PUBLICATIONS

Young et al., "J. Am. Chem. Soc.," vol. 61, pp. 2564 & 2565, (1939).

Simonsen, "The Terpenes," vol. I., pp. 63–65, Cambridge, (1953).

*Primary Examiner*—Donald G. Daus
*Assistant Examiner*—D. B. Springer
*Attorney, Agent, or Firm*—Bacon & Thomas

[57] ABSTRACT

Unsaturated alcohols represented by the general formulas (I) and (II) below

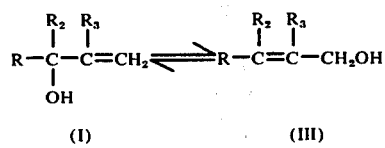

(I)   (III)

wherein R is a substituted or unsubstituted hydrocarbon radical, $R_2$ and $R_3$ are hydrogen or lower alkyl groups, and R and $R_2$ may be linked together are mutually isomerized in the presence of a catalyst comprising a transition metal compound of Groups V, VI and VII of the Mendeleev Periodic Table.

7 Claims, No Drawings

ISOMERIZATION OF THE UNSATURATED ALCOHOLS

BACKGROUND OF THE INVENTION

The present invention relates to the isomerization of unsaturated alcohols, and more particularly to the isomerization in the presence of a transition metal compound of Groups V, VI and VIII of the Mendeleev Periodic Table as the catalyst of unsaturated alcohols described by the following general formulas (I) and (II)

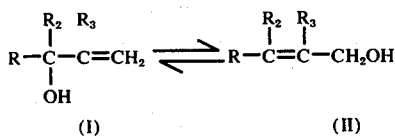

wherein R is a hydrocarbon radical or a substituted hydrocarbon radical, $R_2$ and $R_3$ are hydrogen or lower alkyl groups, and R and $R_2$ may be linked together.

The isomerization reactions of the present invention are equilibrium reactions, and the unsaturated alcohols represented by the general formula (II) may be produced from those of the general formula (I), or conversely, the unsaturated alcohols represented by the general formula (I) may be produced from those of the general formula (II), both processes using the catalysts of the present invention.

As known processes for isomerizing the unsaturated alcohols represented by the general formula (I) into those of the general formula (II), there are exemplified the following:

1. A process of treating the alcohols (I) with a phosphorous halide to give an unsaturated primary halide, reacting it with a salt of an organic acid to give an unsaturated primary ester and hydrolyzing the ester, this process being described in I. N. Nazarov, *Izvest Akad. Nauk S.S.S.R., Otdel, Khim, Nauk*, 1267 (1967).
2. A process of treating the alcohols of formula (I) with acetic anhydride in the presence of an acid to give an unsaturated primary ester, and thereafter hydrolyzing the ester. This process is described in A. I. Fdoseeva, *Sintezy Dashistykh Veshchestv Sbor. State*, 257 (1939).
3. A process of treating the alcohols of formula (I) with acetic anhydride in the presence of a base to give an unsaturated tertiary ester, isomerizing the tertiary ester with an acid to give an unsaturated primary ester and hydrolyzing the ester, as described in W. G. Young, *J. Am. Chem. Soc.* 73:780 (1951); and
4. A process of oxidizing the alcohols of formula (I) to give an αβ-unsaturated aldehyde and selectively reducing the aldehyde, which process is disclosed in M. Stoll, *Helv. Chim. Acta.* 32:1354 (1949).

On the other hand, for the isomerization of the unsaturated alcohols of formula (II) to yield those of formula (I), the following processes are known:

1. Direct isomerization in the presence of an acid catalyst, such as phosphoric acid, sulfuric acid or boron trifluoride, which is reported by Hirao and Kawanaka in "Discussion With Regard to Perfumes", Terpenes and Essential Oil Chemistry, No. 15; Nov. 2, 1971 in Japan; and
2. Halogenation by means of a hydrogen halide or a phosphorous halide followed by hydrolysis, which is described in Laats, Kand Kogerman, A., Easti NSV Tead. Akad. Toim. Keem Geol., 18, (1) 43, (1969).

These known processes, however, have various drawbacks, such as requiring a large number of steps or proceeding with insufficient selectivity in the various reaction steps because of undesirable side reactions.

SUMMARY OF THE INVENTION

It is therefore an object of the present invention to provide an isomerization process which proceeds by an extremely simple reaction sequence.

It is another object of the invention to provide an isomerization reaction which is not subject to the disadvantages of poor selectivity and undesirable side reactions characteristic of known processes of isomerizing unsaturated alcohols.

In accomplishing the foregoing objects, there is provided in accordance with the present invention a process for isomerizing an unsaturated alcohol of the formula (I):

to produce an unsaturated alcohol of the formula (II):

wherein for both formulas R is a saturated or unsaturated aliphatic or cycloaliphatic radical, or a substituted or unsubstituted aromatic or aryl-aliphatic radical, $R_2$ and $R_3$ are hydrogen or lower alkyl radicals and R and $R_2$ may be linked together, as well as isomerizing an unsaturated alcohol of formula (II) to the corresponding unsaturated alcohol of formula (I), wherein the improvement comprises conducting the isomerization reaction in the presence of a transition metal compound of Groups V, VI and VII of the Periodic Table as a catalyst. The preferred catalysts are compounds of vanadium, molybdenum, chromium, tungsten and rhenium, particularly the esters and ammonium salts thereof. The process may be carried out under an atmosphere of air or an oxygen-free medium such as nitrogen, and is typically conducted at a temperature of between 100° and 300° C. A continuous process may be achieved by selectively removing the desired product from the equilibrium mixture.

Other objects, features and advantages of the present invention will become apparent from the detailed description of the invention which follows.

DETAILED DESCRIPTION OF THE INVENTION

The invention is characterized by the use of a transition metal compound of Groups V, VI and VII of the Periodic Table as a catalyst for the topic isomerization process. The esters of transition metal acids, such as vanadic acid, molybdic acid, tungstic acid or perrhenic acid are the preferred catalysts for use in the invention. In particular, the most preferred catalysts in accordance with the invention are orthovanadic acid esters such as methyl orthovanadate, ethyl orthovanadate, n-propyl orthovanadate, isopropyl orthovanadate, n- butyl orthovanadate, isobutyl orthovanadate, sec.-butyl orthovanadate, tert.-butyl orthovanadate, n-pentyl orthovanadate, neopentyl orthovanadate, tert.-pentyl orthovanadate, n-hexyl orthovanadate, cyclohexyl orthovanadate, tetrahydrolinalyl orthovanadate, linalyl orthovanadate and geranyl orthovanadate.

These orthovanadic acid esters can be obtained easily by reacting the corresponding alcohols with ammonium metavandate, vanadium pentoxide or vanadium oxytrichloride. Although the isomerization reaction and synthesis of the catalyst can be performed simultaneously by introducing a vanadium compound such as ammonium metavanadate directly into the reaction system, a vigorous side reaction is caused in such a case. Accordingly, it is preferred to introduce the catalyst in the form of an orthovanadic acid ester, which has been prepared separately, into the reaction system. In this case, various saturated or unsaturated aliphatic or cycloaliphatic alcohols are used to produce the catalyst. The unsaturated alcohols represented by the general formulas (I) and (II) may also be used as a reagent to prepare the catalyst.

Ammonium salts of the transition metal acids described above, or acid anhydrides thereof, such as ammonium metavanadate, ammonium molybdate, ammonium tungstate, ammonium perrhenate, vanadium pentaoxide or vanadium trioxide may also be used as the catalyst of the present invention.

Chelates of the transition metals above, such as vanadyl acetylacetonate $(CH_2COCH_2COCH_3)_2$ VO, vanadium (III) acetylacetonate $(CH_2COCH_2COCH_3)_3$ V, chromium (III) acetylacetonate $(CH_2COCH_2COCH_3)_3$ Cr, manganic acetylacetonate $(CH_2COCH_2COCH_3)_3$ Mn, or molybdenyl acetylacetonate $(CH_2COCH_2-COCH_3)_2$ $MoO_2$ are also suitable.

The amount of the catalyst used in the reaction is usually greater than about 0.001 weight percent, and is preferably in the range of about 0.05 to 3 weight percent based on the weight of the starting alcohol.

The reaction is preferably carried out in the absence of oxygen, for example, in nitrogen atmosphere, but may also be conducted in the presence of air. In the latter case, the selectivity is somewhat decreased.

The reaction is carried out favorably at 100 to 300° C. in general, and preferably in the range of 150 to 200° C.

The reaction pressure is not a critical limitation, and the reaction can be carried out suitably under atmospheric pressure. However, if the boiling point of the starting alcohol or of the resulting alcohol is lower than a preferred reaction temperature, or if the resulting alcohol is expelled from the reaction system by distillation during the reaction, as is described below, it is preferred to control the pressure to an optimum pressure.

Solvents stable under the reaction conditions may be used, but they are not indispensable.

As the isomerization reactions of the subject alcohols are equilibrium reactions, the equilibrium mixture of the starting alcohol and the product alcohol are obtained after completion of the reaction. The equilibrium mixture may be separated by distillation under the reduced pressure conditions. Moreover, certain alcohols, such as geraniol, may be separated by other methods, for example, by preparing the calcium chloride adduct thereof before separation, or by using column-chromatography.

During the isomerization of the unsaturated alcohol represented by the formula (II) to that of (I), the unsaturated alcohol (I) may be obtained nearly quantitatively by expelling the alcohol (I) by means of a suitable distillation tower during the said reaction, since the boiling point of the alcohol (I) is lower than that of the unsaturated alcohol (II). The equilibrium of the system is thereby disturbed because of excess unsaturated alcohol (II), and the equilibrium reaction proceeds mainly in the direction of unsaturated alcohol (I). If the distillation during the reaction is inconvenient, the distillation may be effected under other suitable conditions, such as reduced pressure, after completion of the reaction, with re-cycle of the starting alcohol. Thus, the product may be obtained in nearly quantitative amounts.

The unsaturated alcohols represented by the general formulas (I) and (II), wherein R is a hydrocarbon radical, such as, saturated or unsaturated aliphatic, cyclo aliphatic, aromatic or aryl aliphatic, either substituted or unsubstituted, and wherein $R_2$ and $R_3$ are hydrogen or lower alkyl radicals having up to 4 carbon atoms may be used in the present invention. R and $R_2$ may be linked together, and R may include halogen, hydroxyl, alkoxyl or a carbonyl group as a substituent in the said hydrocarbon radical. Preferably, R consists of an alkyl or a cycloalkyl radical having from 1 to 26 carbon atoms, an alkenyl or a cycloalkenyl radical having from 2 to 36 carbon atoms and up to 9 double bonds or an aromatic or an arylaliphatic radical having from 6 to 26 carbon atoms.

Examples of the unsaturated alcohols by the general formula (I) are 2-methyl-3-butene-2-ol, linalool (3,7-dimethyl-1,6-octadiene-3-ol), 3,7-dimethyl-1-octene-3-ol, 3-ethyl-7-methyl-1,6-octadiene-3-ol, 3,7-dimethyl-7-ethoxy-1-octene-3-ol, 2-benzyl-3-butene-2-ol, nerolidol (3,7,11-trimethyl-1,6,10-dodecatriene-3-ol), isophytol (3,7,11,15-tetramethyl-1-nexadecene-3-ol), 3,7,11,15-tetramethyl-1,6,10,14-hexadecatetraene-3-ol, 1-vinyl cyclohexanol, cyclonerolidol ((5-(2,6,6-trimethyl-1-cyclohexenyl)-3methyl-1-pentene-3-ol)), 1-hexene-3-ol, 3,7-dimethyl-1-octene-3,7-diol, 9-(2,6,6-trimethyl-1-cyclohexenyl)-3,7-dimethyl-1,4,6,8-nonatetraene-3-ol, and 2,3-dimethyl-3-butene-2-ol.

The unsaturated alcohols of general formula (I) may be produced by the known processes, for example, by reacting a carbonyl compound represented by the general formula:

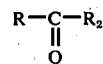

wherein R and $R_2$ correspond to the same substituents of the unsaturated alcohols represented by the general formula (I), with a Grignard's reagent represented by the following formula:

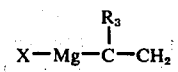

wherein X is halogen and $R_3$ corresponds to the same substituent of the unsaturated alcohols of general formula (I). Moreover, linalool and isophytol are produced by the commercial base as the intermediate of Vitamins A and E.

Examples of the unsaturated alcohols represented by the general formula (II) are crotyl alcohol, prenyl alcohol (3-methyl2-butene-1-ol), geraniol (3,7-dimethyl-2,6-octadiene-1-ol), 3-methyl-7-ethyl-2,6-octadiene-1-ol, 3,7-dimethyl-7-ethoxy-2-octene-1-ol, 3,7-diethyl-2,6-octadiene-1-ol, farnesol (3,7,11-trimethyl-2,6,10-dodecatriene-1-ol), 3-methyl-7,11-diethyl-2,6,10-dodecatriene1-ol, phytol (3,7,11,15-tetramethyl-2-hexadecene-1-ol), 3,7,11,15-tetramethyl-2,6,10,14-hexadecatetraene-1-ol, 3-benzyl-2-butene-1ol and cinnamyl alcohol (3-phenyl-2-propene-1-ol), 2-cyclohexylindene-ethanol, cyclofarnesol ((5-(2,6,6-trimethyl-1-cyclohexenyl)-3-methyl-2-pentene-1-ol)), 2-hexene-1-ol, 3,7-dimethyl-2,6-octadiene-1,7-diol, Vitamin A (retinol), and 2,3-dimethyl-2-butene-1-ol.

When R represents the $R_1$-$CH_2$-radical and $R_3$ is hydrogen in the general formulas (I) and (II), the process of the invention may be represented as follows:

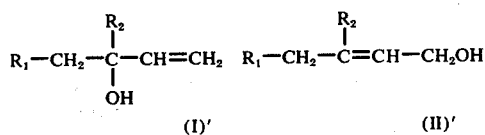

(I)'  (II)' wherein $R_1$ is hydrogen, a saturated or unsaturated aliphatic or cycloalphatic radical, an aromatic radical or an arylaliphatic radical having up to 25 carbon atoms, either substituted or unsubstituted. The unsaturated primary alcohols represented by the general formula (II)' are useful products of the present invention.

The unsaturated alcohols obtained by the present invention are well known in part. For example, they are valuable compounds as perfumes, or as intermediates for the preparation of perfumes, medicines and agricultural chemicals. More particularly, geraniol, where R is

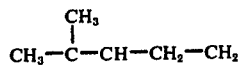

$R_2$ is methyl and $R_3$ is hydrogen in the general formula (II), and nerol which is the stereo isomer of geraniol, may be commercially produced by the process of the invention from linalool, which is represented by the general formula (I) where R, $R_2$ and $R_3$ are the same as in geraniol.

Recently, linalool has been synthesized at quite a low cost as an intermediate product of the preparation of vitamin A and vitamin E, since the synthesis of these vitamins has been developed successfully. However, the processes for the preparation of its isomer, i.e., geraniol, which is very important as a terpene perfume and of its geometrical isomer, nerol, at a low cost have never been developed. At present, they are extracted from natural essential oil or semisynthesized from pinene.

Many processes have been proposed for obtaining geraniol or nerol by isomerizaton of linalool. However, they could not be performed on a commercial scale owing to various problems such as selectivity of the reaction, number of steps and cost of chemicals used. According to the process of the present invention, surprisingly, the disadvantages of the known processes can be eliminated, and linalool can be isomerized into geraniol and nerol in one step and in a high yield. Geraniol or nerol may be produced by isomerizing linalool in the presence of the esters of orthovanadate at high temperature. Although the reaction may be carried out in air, it is preferred to carry out the reaction in the absence of oxygen, for example, in a nitrogen atmosphere. The reaction temperature may be in the range of 100 – 300° C. in general. From a viewpoint of reaction velocity or thermal stability of the reaction components, the preferred temperature is in the range of 150°– 250° C. Concentration of the catalyst is in the range of 0.01 – 3 wt. percent, though a low concentration of about 10 ppm. may also be employed with success. Reaction pressure is not particularly important and the reaction can generally be carried out suitably under atmospheric pressure. The isomerization reaction is an equilibrium reaction and the resulting product is an equilibrium mixture of linalool, geraniol and nerol. Therefore, geraniol and nerol must be removed from the mixture. If the resulting mixture is distilled in the presence of the catalyst, linalool, having the lowest boiling point, is expelled first to break the quilibrium thereby reducing the yield of the desired product. Consequently, the distillation must be carried out at a low temperature at which the isomerization reaction hardly occurs. However, it is substantially impossible to perform the distillation while the liquid temperature is kept low enough not to cause the isomerization in view of the pressure drop caused by the number of distillation steps required for fractional distillation of geraniol or nerol from linalool. For solving this problem, a technique to be described below is used in the present invention.

The relative volatility of the catalyst is far lower than that of even geraniol which has the highest boiling point of the reaction products. Therefore, the catalyst can be separated easily by simple distillation. The starting compound and the reaction products can be separated from the catalyst by distilling the reaction liquid in a distillation tower of the type wherein the pressure drop is very small at a temperature which is lower than the reaction temperature by about 50° – 150° C. (this varies depending upon reaction temperature and catalyst concentration). The reaction liquid from which the catalyst has thus been removed is then subjected to rectification by using a distillation tower having a sufficient number of steps. Thus, geraniol and nerol can be separated from linalool without notable occurrence of the isomerization reaction. The catalyst and linalool thus separated can be recycled again to the reaction system and conversion can be raised to nearly 100% even by the equilibrium reaction.

It is more advantageous to add a high boiling solvent such as polyethylene glycol, which is separable according to simple distillation and which has a far higher boiling point than that of geraniol, so as to prevent concentration of the catalyst during the catalyst separation procedure, to increase the amount of geraniol expelled and to increase the capacity of the catalyst separation. Said high boiling solvents may be incorporated previously in the reaction system.

In view of the uses of geraniol and nerol, the high boiling solvents used in the present invention should satisfy, in addition to the above described conditions, some other conditions, namely, they should not severely swell, they should be soluble in linalool, geraniol, nerol and orthovanadic acid ester catalysts to form a stable solution and they themselves should be stable under the isomerization reaction conditions. The term "stable" herein does not exclude ester exchange reaction with the catalyst. Any high boiling solvent that satisfies the conditions may be used. Preferred solvents are high boiling alcohols such as stearyl alcohol, cetyl alcohol or polyethylene glycol and high boiling hydrocarbons such as squalane or paraffin oil. Though no particular limitation is provided with respect to quantity of the solvents, 5 – 100 wt. percent based on the total weight of the reaction liquid is preferred in view of quantity of geraniol expelled, the capacity of separation of the catalyst and the capacity of the reaction vessel.

The product obtained by the above described process is a mixture of 60 – 65% of geraniol and 35 – 40% of nerol. Though the product can be used directly as a perfume or the like, in order to obtain a higher purity of geraniol or nerol, further separation of the products is necessary. The separation is effected by rectification, a technique involving the calcium chloride adduct, column chromatography, etc. If geraniol only is desired, nerol is separated and recycled into the reaction system to cause the isomerication reaction in the direction of geraniol, thereby forming a mixture of linalool, geraniol and nerol. Thus, a reduction in yield is hardly caused. On the other hand, if nerol is desired, geraniol is separated and recycled into the reaction system, thus eliminating reduction in yield. Geraniol and nerol obtained according to the present invention have a great value as perfumes or as intermediate products for the preparation of perfumes and medical supplies.

The process of the invention may be applicable to produce the unsaturated alcohols represented by the general formula (II) from those of the general formula (I) in the same manner as illustrated to produce geraniol or nerol from linalool.

The following examples are presented to more fully illustrate the present invention, it being understood that the same are not to be construed as being in any way limitative. The Examples 1 to 25 which follow illustrate how the invention may be carried out to transform the unsaturated alcohols represented by the general formula (I) to those of the formula (II).

Example 1

In a hermetically sealed reactor in which the air is substituted by nitrogen, 400g of linalool (3,7-dimethyl-1,6-octadiene-3-01)is reacted with cyclohexyl orthovanadate (2g) at 150° C. for 4 hours, and the reaction mixture is subjected to steam distillation. The distillates are separated to give an oily layer and an aqueous layer. The aqueous layer is extracted with n-hexane and the n-hexane layer is combined with the oily layer. The mixture is dried over anhydrous sodium sulfate and distilled under reduced pressure to give 111g of a mixture of geraniol and nerol (3,7-dimethyl-2,6-octadiene-1-01) together with raw linalool (275 g). The conversion is 31.2%, and the selectivity is 89%.

Example 2

In a hermetically sealed reactor in which the air is substituted by nitrogen, a mixture of linalool (10g), tetralin (10g) and cyclohexyl orthovanadate (0.1g) is reacted at 150° C. for 8hours. The reaction mixture is analyzed by the gas chromatography, whereby it is confirmed that the reaction mixture contains linalool (69.3% by weight) and a mixture (28.7% by weight) of geraniol and nerol in tetralin. The conversion is 30.7% and the selectivity is 93%.

Example 3

In a hermetically sealed reactor in which the air is substituted by nitrogen, a mixture of linalool (10g), tetralin (10g) and secbutyl orthovanadate (0.1g) is reacted at 160° C. for 6 hours. The reaction mixture is analyzed by gas chromatography. Thus, it is confirmed that the reaction mixture contains linalool (77.0%) and a mixture 18.0% of geraniol and nerol in tetralin. The conversion is 23.0%, and the selectivity is 78%.

Example 4

In a hermetically sealed reactor in which the air is substituted by nitrogen, a mixture of linalool (10g), tetralin (10g) and tert-butyl orthovanadate (0.1g) is reacted at 150° C. for 5 hours. The reaction mixture is analyzed by gas chromatography. Thus, it is confirmed that the reaction mixture contains linalool (73.6%) and a mixture 25.2% of geraniol and nerol. The conversion is 26.4%, and the selectivity is 95%.

Example 5

In a hermetically sealed reactor in which the air is substituted by nitrogen, a mixture of linalool (10g), tetralin (10g) and isobutyl orthovanadate (0.1g) is reacted at 140° C. for 4 hours. The reaction mixture is analyzed by gas chromatography. It is confirmed that linalool (80.3%)and a mixture 16.3% of geraniol and nerol are contained therein. The conversion is 19.7%, and the selectivity is 83%.

Example 6

A mixture of linalool (10g), ammonium metavanadate (0.1g) and cyclohexanol (1g) is reacted at 140° C. for 7 hours in a nitrogen atmosphere. The reaction mixture is filtered, and the filtrate is analyzed by gas chromatography. It is confirmed that linalool (69.4%) and a mixture 14.9% of geraniol and nerol are contained therein. The conversion is 30.6%, and the selectivity is 49%.

Example 7

A mixture of linalool (10g) and isobutyl orthovanadate (0.1g) is reacted at 110° C. for 7 hours in the atmosphere. The reaction mixture is analyzed by gas chromatography. It is confirmed that linalool (75%) and a mixture (10.2%) of geraniol and nerol are contained therein. The conversion is 25%, and the selectivity is 41%.

Example 8

A mixture of linalool (10g), tetralin (10g) and cyclohexyl orthovanadate (0.1g) is heated at 150° C. for 8 hours under atmospheric conditions. The reaction mixture is analyzed by gas chromatography, whereby it is confirmed that linalool (73.8%) and a mixture (14.2%) of geraniol and nerol are contained therein. The conversion is 26.2%, and the selectivity is 54%.

Example 9

In a hermetically sealed reactor in which the air is substituted by nitrogen, a mixture of 10g of nerolidol (3,7,11-tri-methyl-1,6,10-dodecatriene-3-01) and tert-butyl orthovanadate (0.1g) is reacted at 150° C. for 4 hours. The reaction mixture is analyzed by gas chromatography. It is confirmed that nerolidol (85.7%) and farnesol (3,7,11-trimethyl-2,6,10-dodecatriene-1-

10(12.2%) are contained therein. The conversion is 14.3%, and the selectivity is 85%.

Example 10

In a hermetically sealed stainless reactor, a mixture of 2-methyl-3-butene-2-01 (10g) and cyclohexyl orthovanadate (0.1g) is reacted at 150° C. for 3 hours. The reaction mixture is analyzed by gas chromatography. It is confirmed that 2-methyl-3-butene-2-01 (86.9%) and 3-methyl-2-butene-1-01 (9.8%) are contained therein. The conversion is 13.1%, and the selectivity is 75%.

(59.2%) and 3-ethyl-7-methyl-2,6-octadiene-1-ol (29.0%) are contained therein. The conversion is 41.8%, and the selectivity is 71%.

Examples 14 to 25

Said examples are carried out under the conditions described in the following Table 1 and the results obtained are described in the same table. All of the reactions are carried out under an atmosphere of nitrogen. Examples 16 and 21 are carried out at greater than atmospheric pressure. The compositions of the product alcohols are measured by gas-chromatography.

Table 1

| | Starting Alcohol | | Catalyst | Reaction Temp. (°C) | Reaction Time | Product Alcohol | | Conversion (%) | Selectivity (%) |
|---|---|---|---|---|---|---|---|---|---|
| 14 | Linalool | 30g | (i-BuO)₃VO: 0.03g | 200 | 3 hrs | Geraniol<br>Nerol | 24.7%<br>15.7% | 41.9 | 96.4% |
| 15 | Linalool | 30g | (i-BuO)₃VO: 0.03g | 190 | 4 hrs. | Geraniol<br>Nerol | 22.6%<br>14.4% | 37.6 | 98.4 |
| 16 | Linalool | 30g | (n-PrO)₃VO: 0.03g | 230 | 1 " | Geraniol<br>Nerol | 23.8%<br>14.6% | 40.0 | 96.0 |
| 17 | Linalool | 100g | (n-Pro)₃VO: 0.01g | 250 | 3 " | Geraniol<br>Nerol | 20.1%<br>12.4% | 39.4 | 82.5 |
| 18 | Linalool | 20g | (acac)₂VO: 0.04g | 200 | 3 " | Geraniol<br>Nerol | 24.0%<br>14.9% | 41.6 | 93.5 |
| 19 | Linalool | 20g | (acac)₃V: 0.04g | 200 | 3 " | Geraniol<br>Nerol | 24.9%<br>15.1% | 44.2 | 90.5 |
| 20 | Isophytol | 20g | (i-BuO)₃VO: 0.05g | 180 | 6.5 " | Phytol | 22.1% | 23.7 | 93.2 |
| 21 | 3-butene-2-ol | 20g | (i-BuO)₃VO: 0.1g | 160 | 3 " | Crotyl alcohol | 16.8% | 18.7 | 89.8 |
| 22 | 1-vinyl cyclohexanol | 20g | (i-BuO)₃VO: 0.1g | 160 | 3 " | 2-cyclohexylidene ethanol | 13.5% | 15.0 | 90.0 |
| 23 | 1-phenyl-2-propene-1-ol | 20g | (i-BuO)₃VO: 0.02g | 180 | 5 " | Cinnamyl alcohol | 34.1% | 35.2 | 96.9 |
| 24 | Linalool | 25g | (acac)₃Cr: 0.05g | 195 | 3 " | Geraniol<br>Nerol | 4.3%<br>2.5% | 17.9 | 38.0 |
| 25 | Cyclonerolidol | 20g | (i-BuO)₃VO: 0.04g | 200 | 1 " | Cyclofarnesol | 35.4% | 38.0 | 93.2 |

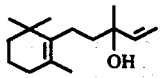 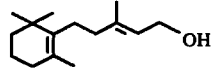

Example 11

In a hermetically sealed reactor in which the air is substituted by nitrogen, a mixture of linalool (10g) and isobutyl molybdate (0.1g) is reacted at 160° C. for 6 hours. The reaction mixture is analyzed by gas chromatography. It is confirmed that linalool (81.0%) and a mixture (5.9%) of geraniol and nerol are contained therein. The conversion is 19.0%, and the selectivity is 31%.

Example 12

A mixture of linalool (10g), ammonium perrhenate (0.05g) and tetrahydrolinalool (1g) are reacted at 150° C. for 5 hours in a nitrogen atmosphere. The reaction mixture is analyzed by gas chromatography. It is confirmed that linalool (84%) and a mixture (4.5%) of geraniol and nerol are contained therein. The conversion is 16%, and the selectivity is 28%.

Example 13

In a hermetically sealed reactor in which the air is substituted by nitrogen, a mixture of 3-ethyl-7-methyl-1,6-octadiene-3-ol (10g) and tert-butyl orthovanadate (0.025g) is reacted at 180° C. for 3 hours. The reaction mixture is analyzed by gas chromatography. It is confirmed that raw 3-ethyl-7-methyl-1,6-octadiene -3-ol In Table 1, the catalyst (i-BuO)₃VO means isobutyl orthovanadate, (n-PrO)₃VO means n-propyl orthovanadate, (acac)₂VO means vanadyl acetylacetonate, (acac)₃V means vanadium (III) acetylacetonate and (acac)₃Cr means chromium (III) acetylacetonate.

The Examples 26 to 29 which follow show how the invention may be carried out to produce geraniol or nerol from linalool.

Example 26

Isomerization and purification:

In a nitrogen-replaced, closed vessel 400g of linalool and 100g of isobutyl orthovanadate were charged reacted under heating at 180° C. for 3 hours. The reaction liquid was analyzed according to gas chromatography to confirm that 63.1% linalool. 22.8% geraniol and 13.4% nerol were contained therein. 100.5 grams of the reaction liquid were taken, placed in a distillation apparatus provided with a Biglew column and distilled under 0.5 mmHg to expel nearly all the contents. The highest temperature of the liquid during this procedure was 75° C. Total weight of the distillate was 96g which was confirmed to comprise 62.9g of linalool, 18.6g of geraniol and 13.4g of nerol according to gas chromatography. The distillation residue was also confirmed in the same manner to contain 3.8g of geraniol and traces of linalool and nerol. The distillate was further subjected to rectification to obtain 62.0g of linalool and 31.5g of geraniol and nerol (comprising 58.1% of geraniol and 41.4% of nerol). Reuse of the catalyst:

The residue of the first distillation was added to 100g of linalool and the mixture was reacted at 180° C. for 3 hours in a nitrogen-replaced, closed vessel. The reaction liquid was analyzed according to gas chromatography to confirm that 68.4% linalool, 18.8% geraniol and 11.1% nerol were contained therein.

Example 27

150 grams of the first reaction liquid of Example 1 (containing 63.1% linalool, 22.8% geraniol and 13.4% nerol) were added to 15.0g of polyethylene glycol and the whole was subjected to distillation by using a Biglew column under a reduced pressure of 0.35 mmHg. The distillate (145g) obtained at a temperature below 67° C. was confirmed to contain 67.5% linalool, 19.2% geraniol and 12.8% nerol.

The distillation residue was reacted with 150g of linalool in a nitrogen-replaced, closed vessel at 195° C. for 2 hours and the product was distilled under the same conditions as above. These procedures wee repeated four times.

Compositions of the distillates are shown in Table 2 below:

Table 2

|  | Total | Linalool (wt.%) | Geraniol (wt.%) | Nerol (wt.%) |
|---|---|---|---|---|
| The first distillate | 145 g | 67.5% | 19.2% | 12.8% |
| The second distillate | 132 g | 77.6% | 11.5% | 9.4% |
| The third distillate | 145 g | 73.7% | 15.5% | 9.8% |
| The fourth distillate | 145 g | 65.6% | 20.1% | 13.6% |

Example 28

Recycle of linalool and nerol (preparation of pure geraniol):

In a nitrogen-replaced, closed vessel, 235g of linalool, 0.55g of n-propyl orthovanadate and 40g of polyethylene glycol were charged and reacted under heating at 190°–193° C. for 2 hours. The reaction liquid was distilled by using a Biglew column under a reduced pressure of 0.5 mmHg to obtain 225g of distillate and 45g of distillation residue. The distillate was rectified further to obtain 138g of linalool (containing 93.5% linalool, 1.8% geraniol and 2.5% nerol). 32.5g of nerol (containing 95.2% nerol and 4.5% of geraniol) and 41.5g of geraniol (containing 97.2% of geraniol and 2.5% of nerol).

238 grams of linalool and 32.5g of nerol both obtained by the rectification were added to an additional 50g of linalool and the mixture was added to 45g of the residue of the first distillation. The whole mixture was heated at 190° C. to effect the reaction for 2 hours. The reaction liquid was subjected to the procedures for separation of the catalyst, separation of the high boiling solvent and rectification in the same manner as above to obtain 134g of linalool (containing 94.1% linalool, 1.2g geraniol and 1.9% nerol), 30.7g of nerol (containing 94.2% nerol and 4.9% geraniol) and 40.3g of geraniol (containing 97.6% geraniol and 2.0% nerol).

Example 29

Recycle of linalool and geraniol (preparation of pure nerol):

In a nitrogen-replaced, closed vessel, 300g linalool, 0.3g of sec.-butyl orthovanadate and 50g of polyethylene glycol were charged and heated at 200° C. to effect the reaction for three hours. The reaction liquid was subjected to the separation and rectification in the same manner as in Example 28 to obtain 56g of distillation residue (residue of the first distillation), 181g of linalool (containing 93.6% linalool, 1.6% geraniol and 2.8% nerol), 43.2g of nerol (containing 96.4% nerol and 3.0% geraniol) and 59.8g of geraniol (containing 95.1% geraniol and 4.5% nerol).

181 grams of linalool and 59.8g of geraniol both obtained by the rectification were added to an additional 55g of linalool and the mixture was added to 56g of the residue of the first distillation. The whole mixture was heated at 200° C. to effect the reaction for 3 hours. The reaction liquid was subjected to the catalyst separation and rectification procedures in the same manner as above to obtain 178g of linalool (containing 93.2% linalool, 1.4% geraniol and 2.3% nerol), 42.8g of nerol (containing 95.4% nerol and 3.9% geraniol) and 58.9g of geraniol (containing 96.0% geraniol and 3.4% nerol).

Examples 30 to 43, which follow, show how the invention may be carried out to produce the unsaturated alcohols represented by the general formula (I) from those of the formula (II).

Example 30

In a three-neck distillation flask provided with a distillation tower, 40g of geraniol, 0.1g of isobutyl orthovanadate and 40g of polyethylene glycol were charged. After sufficient replacement with nitrogen in the reaction system, the liquid mixture was heated to 180° C. The reaction was carried out under rectification, while the pressure at the top of the tower was kept at 100 – 200 mmHg. The reaction was continued until the distillation was completed to obtain 36g of linalool as distillation fraction (yield 90%). The purity of the linalool was 98.5%.

Example 31

In a nitrogen-replaced autoclave, 20g of crotyl alcohol and 0.1g of n-propyl orthovanadate were reacted under heating at 160° C. for 3 hours. The liquid reaction mixture was analyzed according to gas chromatography to confirm that 81% of crotyl alcohol and 17.4% of 3-butene-2-ol were contained therein. This result corresponds to a conversion of 19% and a selectivity coefficient of 91.6%.

Example 32

In a nitrogen-replaced autoclave, 20g of prenyl alcohol (3-methyl-2-butene-1-ol) and 0.1g of n-butyl orthovanadate were reacted under heating at 160° C for 3 hours. The liquid reaction mixture was analyzed according to gas chromatography to confirm that 7.5% of prenyl alcohol and 23% of 2-methyl-3-butene-2-ol were contained therein.

This result corresponds to a conversion of 25% and a selectivity coefficient of 95%.

Example 33

In a three-neck distillation flask provided with a distillation tower, 40g of farnesol, 0.05g of sec.-butyl orthovanadate and 20g of polyethylene glycol were charged. After replacement with nitrogen, the liquid mixture was heated to 210° C. The reaction was carried out under rectification, while the pressure at the top of the tower was controlled at between 50 – 100mmHg. The reaction was continued until the distillation was completed to obtain 37.2g of nerolidol (purity 96.5%) as distillation fraction.

Example 34

In a nitrogen-replaced, closed vessel, 40g of phytol and 0.05g of isopropyl orthovanadate were reacted under heating at 210° C for 1 hour. The reaction liquid was analyzed according to gas chromatography to confirm that 57% of phytol and 40% of isophytol were contained therein. This result corresponds to a conversion of 43% and a selectivity coefficient of 93%.

Example 35

In a nitrogen-replaced, closed vessel, 20g of geraniol and 0.05g of tert.-butyl orthovanadate were reacted under heating at 180° C for 6 hours. The reaction liquid was analyzed according to gas chromatography to confirm that 40.8% of geraniol (containing nerol) and 56.7% of linalool were contained therein. This corresponds to conversion of 59.2% and selectivity coefficient of 96.4%.

Example 36

In a nitrogen-replaced, closed vessel, 40g of geraniol and 0.04g of isobutyl orthovanadate were reacted at 250° C for 30 minutes. The reaction liquid was analyzed according to gas chromatography to confirm that 43.5% geraniol (containing nerol) and 52.1% linalool were contained there. This result corresponds to a conversion of 56.5% and a selectivity coefficient of 92.2%.

Example 37

In a nitrogen-replaced, closed vessel, 20g of 3,7-diethyl-2,6-octadiene-1-ol and 0.05g of cyclohexyl orthovanadate were reacted at 195° C for 1 hour. The reaction liquid was analyzed according to gas chromatography to confirm that 47.5% of 3,7-diethyl-2,6-octadiene-3-ol were contained therein. This corresponds to a conversion of 52.4% and a selectivity coefficient of 97.1%.

Example 38

In a reaction vessel provided with a reflux condenser were charged 30g of geraniol, 0.05g of ammonium metavandate and 2g of cyclohexanol. After nitrogen-replacement, the mixture was heated to 150° C while nitrogen was introduced slowly therein to effect the reaction for 5 hours, the resulting ammonia and water being expelled from the reaction system. The reaction liquid was analyzed according to gas chromatography to confirm that 38.1% geraniol (containing nerol) and 29.0% linalool were contained therein. This corresponds to a conversion of 61.9% and a selectivity coefficient of 46.8%.

Example 39

In a nitrogen-replaced, closed vessel, 20g of geraniol and 0.04g of isopropyl tungstate were charged and the mixture was reacted under heating at 160° C for 5 hours. The reaction liquid was analyzed according to gas chromatography to confirm that 39.4% geraniol (containing nerol) and 20.7% linalool were contained therein. This corresponds to a conversion of 60.6% and a selectivity coefficient of 34.1%.

Examples 40 to 43

Examples 40 to 43 are carried out under the conditions described in the following Table 3 and the results obtained are described in the same table. All of the reactions are carried out under an atmosphere of nitrogen. Example 40 is carried out under a compressed atmosphere.

The compositions of the product alcohols are measured by gas-chromatography.

The abbreviated words of the catalysts in Table 3 are the same as in Table 1.

Table 3

| | Starting Alcohol | Catalyst | Reaction Temp. (° C) | Reaction Time (hr) | Product Alcohol | Conversion (%) | Selectivity |
|---|---|---|---|---|---|---|---|
| 40 | 2,3-dimethyl-2-butene-1-ol | 20g (i-BuO)$_3$VO: 0.1g | 160 | 3 hrs. | 2,3-dimethyl-3-butene-2-ol | 18% | 19.7 | 91.4 |
| 41 | geraniol | 20g (acac)$_2$VO: 0.04g | 200 | 3 hrs. | linalool nerol | 55.1% 13.5% | 59.2 | 93.1 |
| 42 | farnesol | 30g (acac)$_3$V: 0.06g | 200 | 2 hrs. | nerolidol | 52.7% | 57.6 | 91.5 |
| 43 | geranylgeraniol | 30g (i-BuO)$_3$VO: 0.03g | 200 | 3 hrs. | geranyl-linalool | 39.0% | 42.3 | 92.2 |

Whereas the present invention has been described and pointed out with reference to several preferred embodiments thereof, it is to be understood that the scope of the proprietary rights resulting from this application are to be limited only by the claims appended hereto.

What is claimed is:

1. In a process for preparing a mixture of geraniol and nerol which comprises the steps of isomerizing linalool in the presence of an orthovanadic acid ester catalyst wherein the ester moiety thereof is derived from a $C_1 - C_{10}$ alkyl, cycloalkyl or alkenyl alcohol at about 100° to 300° C and distilling the reaction mixture consisting of geraniol, nerol, unreacted linalool and the catalyst under reduced pressure to remove unreacted linalool and the catalyst therefrom the improvement comprising distilling said reaction mixture under reduced pressure in the presence of a high boiling solvent to separate said catalyst from said reaction mixture to form a distillate mixture consisting of geraniol, nerol and unreacted linalool, and a bottom mixture consisting of said catalyst with said high boiling solvent, rectifying said distillate mixture of geraniol, nerol and unreacted linalool, to remove said unreacted linalool therefrom to obtain a mixture of geraniol and nerol.

2. The process as defined in claim 1, further comprising the steps of separating said geraniol from said nerol, recovering said geraniol and recycling said nerol.

3. The process as defined in claim 2, further comprising the steps of separating said nerol from said geraniol, recovering said nerol and recycling said geraniol.

4. The process as defined in claim 1, wherein said high boiling solvent is a high boiling alcohol.

5. The process as defined in claim 1, wherein said high boiling solvent is selected from the group consisting of stearyl alcohol, cetyl alcohol and polyethylene glycol.

6. The process as defined in claim 1, wherein said high boiling solvent is incorporated in the reaction system prior to said isomerization step.

7. The process as defined in claim 1, wherein the recovered catalyst and unreacted linalool are recycled in the reaction system.

* * * * *